(12) United States Patent
Han et al.

(10) Patent No.: US 11,767,226 B2
(45) Date of Patent: *Sep. 26, 2023

(54) CO-PRODUCTION OF METHANOL, AMMONIA AND UREA

(71) Applicant: Haldor Topsøe A/S, Kgs. Lyngby (DK)

(72) Inventors: Pat A. Han, Smørum (DK); Mitra Heidarpanah, Nærum (DK)

(73) Assignee: Topsoe A/S, Kgs. Lyngby (DK)

( * ) Notice: Subject to any disclaimer, the term of this patent is extended or adjusted under 35 U.S.C. 154(b) by 0 days.

This patent is subject to a terminal disclaimer.

(21) Appl. No.: 17/408,667

(22) Filed: Aug. 23, 2021

(65) Prior Publication Data

US 2021/0380427 A1    Dec. 9, 2021

Related U.S. Application Data

(62) Division of application No. 16/467,192, filed as application No. PCT/EP2018/055648 on Mar. 7, 2018, now Pat. No. 11,130,680.

(30) Foreign Application Priority Data

Mar. 12, 2017  (DK) .......................... PA 2017 00172

(51) Int. Cl.
    *C01C 1/04*    (2006.01)
    *C07C 29/15*   (2006.01)
    (Continued)

(52) U.S. Cl.
    CPC .......... *C01C 1/0488* (2013.01); *B01J 8/0457* (2013.01); *B01J 8/0492* (2013.01); *B01J 8/0496* (2013.01);
    (Continued)

(58) Field of Classification Search
    None
    See application file for complete search history.

(56) References Cited

U.S. PATENT DOCUMENTS

| 4,315,900 A | 2/1982 | Nozawa et al. |
| 4,407,973 A | 10/1983 | van Dijk |

(Continued)

FOREIGN PATENT DOCUMENTS

| EP | 0212758 A2 * | 3/1987 | ............ C01B 3/382 |
| EP | 2 192 082 B1 | 7/2013 | |

(Continued)

OTHER PUBLICATIONS

Integration of Urea-Formaldehyde Production, Boosting Profitability for Urea Producers, 6th GPCA Fertilizer Convention, Dubai, Sep. 14-16, 2015, Retrieved from Internet <URL: http://gpcafertilizers.com/2015/wp-content/uploads/2015/10/Haldor-Topsoe-David-James-Bray.pdf>.

*Primary Examiner* — Jennifer A Leung
(74) *Attorney, Agent, or Firm* — BLANK ROME LLP

(57) ABSTRACT

A process and plant for the co-production of methanol and ammonia together with urea production from a hydrocarbon feed without venting to the atmosphere carbon dioxide captured from the methanol or ammonia synthesis gas and without using expensive air separation units and water gas shift. Carbon dioxide is removed from flue gas from reforming section and used to convert partially or fully all ammonia into urea.

8 Claims, 1 Drawing Sheet

(51) Int. Cl.
*C07C 29/152* (2006.01)
*C01B 3/34* (2006.01)
*C07C 273/04* (2006.01)
*C07C 273/10* (2006.01)
*C01B 3/02* (2006.01)
*C07C 29/151* (2006.01)
*B01J 8/04* (2006.01)

(52) U.S. Cl.
CPC ............ *C01B 3/025* (2013.01); *C07C 29/152* (2013.01); *C07C 29/1518* (2013.01); *C07C 273/04* (2013.01); *C07C 273/10* (2013.01); *B01J 2208/00548* (2013.01); *B01J 2219/0004* (2013.01); *B01J 2219/00038* (2013.01); *C01B 2203/061* (2013.01); *C01B 2203/068* (2013.01); *C01B 2203/141* (2013.01); *C01B 2203/142* (2013.01)

(56) References Cited

U.S. PATENT DOCUMENTS

| | | | |
|---|---|---|---|
| 7,947,747 B2 * | 5/2011 | Xie | ........................ C07C 29/152 |
| | | | 518/715 |
| 8,303,923 B2 * | 11/2012 | Han | .................... C07C 29/1518 |
| | | | 518/703 |
| 10,550,076 B2 * | 2/2020 | Erlandsson | ........... C01C 1/0405 |
| 2013/0095029 A1 | 4/2013 | Han | |
| 2018/0072658 A1 | 3/2018 | Erlandsson | |
| 2021/0380428 A1 * | 12/2021 | Han | ........................ B01J 8/0496 |

FOREIGN PATENT DOCUMENTS

| | | | | |
|---|---|---|---|---|
| EP | 2 805 914 A1 | 11/2014 | | |
| EP | 2818458 A1 * | 12/2014 | .......... | B01J 19/1856 |
| WO | WO-02/096845 A2 | 12/2002 | | |
| WO | WO-02/096845 A2 | 12/2002 | | |
| WO | WO-2011/160745 A1 | 12/2011 | | |
| WO | WO-2014/012601 A1 | 1/2014 | | |
| WO | WO-2016/132091 A1 | 8/2016 | | |
| WO | WO-2017/025272 A1 | 2/2017 | | |

* cited by examiner

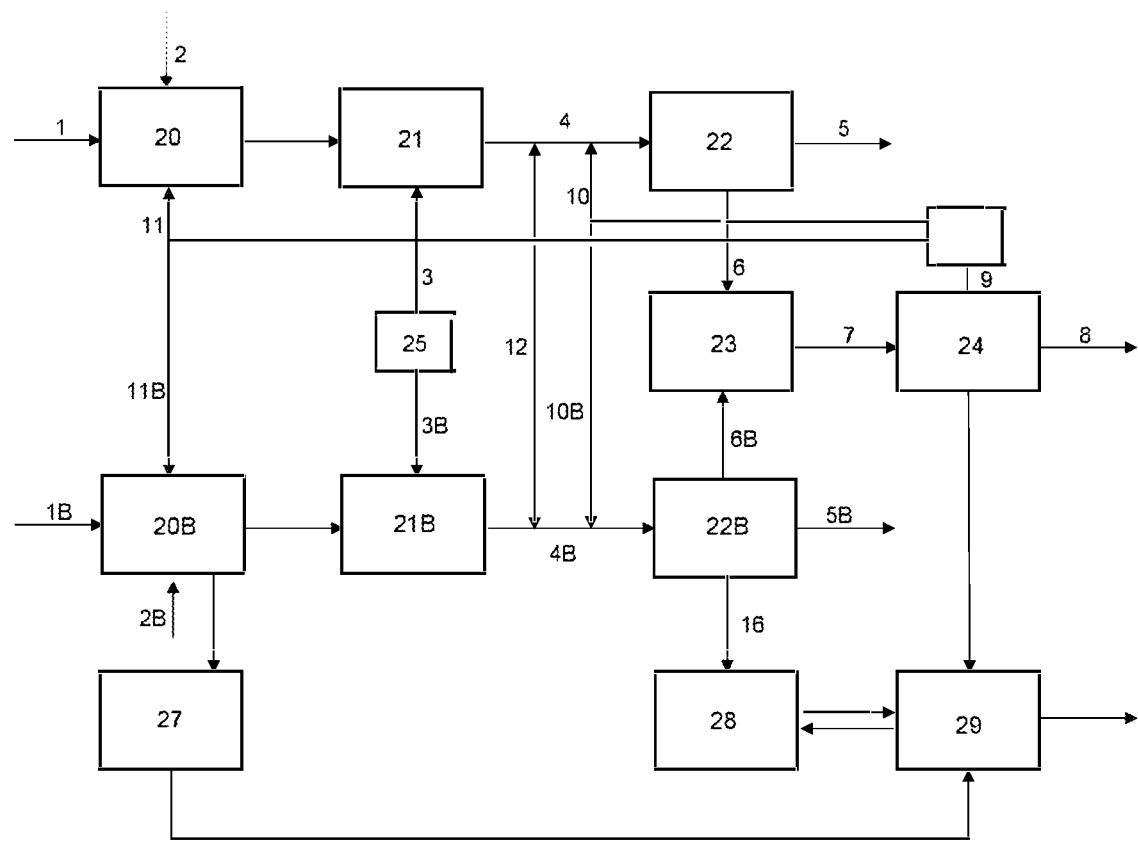

CO-PRODUCTION OF METHANOL, AMMONIA AND UREA

CROSS-REFERENCE TO RELATED APPLICATIONS

This is a divisional of U.S. patent application Ser. No. 16/467,192, filed Jun. 6, 2019, which is a national stage of PCT/EP2018/055648, filed Mar. 7, 2018, which claims priority to Denmark Application No. PA 2017 00172, filed Mar. 12, 2017, the disclosures of which are incorporated by reference in their entireties herein.

FIELD OF THE INVENTION

The present invention relates to a process for the co-production of methanol and ammonia from a hydrocarbon feed without venting to the atmosphere carbon dioxide captured from the methanol and ammonia synthesis gas and without using expensive water gas shift and carbon dioxide removal steps. More particularly the invention is concerned with a sequential and once-through (single pass) process for the co-production of methanol and ammonia without water gas shift and carbon dioxide removal and without air separation unit used in the reforming section of the plant.

BACKGROUND OF THE INVENTION

Current processes for co-production of methanol and ammonia involve generally parallel processes in which a common reforming section is used to generate a synthesis gas which is split in separate parallel streams, one of which is used for methanol synthesis and the other for ammonia synthesis. The co-production of methanol and ammonia can also be conducted sequentially or in series, where the synthesis gas produced in the reforming section is first converted to methanol and the unreacted gas containing carbon oxides and hydrogen is subsequently used for ammonia synthesis. Water gas shift and/or carbon dioxide removal steps of the synthesis gas stream are required, thus involving the release of $CO_2$ to the atmosphere and the investment in highly expensive and complicated units for conducting the shift conversion and carbon dioxide removal.

SUMMARY OF THE INVENTION

In a first aspect of the present invention is provided a process for co-producing methanol, ammonia and urea which is simpler than current process and which at the same time enables minimum release of carbon dioxide to the atmosphere.

In a second aspect of the present invention is provided a process for co-producing methanol, ammonia and urea which allows the optimized use of two parallel methanol production lines.

These and other advantages are achieved by the present process for co-producing methanol, ammonia and urea from a hydrocarbon feedstock, said process comprising the steps of:

a) from a first methanol processes, comprising a first reforming step and first methanol conversion step obtaining a first effluent comprising methanol and a first gas effluent comprising nitrogen, hydrogen and unconverted carbon oxides, and from a second methanol processes, comprising a second reforming step and a second methanol conversion step obtaining a second effluent comprising methanol and a second gas effluent comprising nitrogen, hydrogen and unconverted carbon oxides b) producing an ammonia synthesis gas from the first and/or second gas effluent comprising nitrogen, hydrogen and unconverted carbon oxides in a common catalytic methanation stage and withdrawing said ammonia synthesis gas preferably having a $H_2:N_2$ molar ratio of 3:1;

c) catalytically converting the nitrogen and hydrogen of the ammonia synthesis gas in a common ammonia synthesis stage and withdrawing an effluent comprising ammonia and an off-gas stream comprising hydrogen, nitrogen and methane, and d) reacting at least part of the effluent comprising ammonia with at least part of a flue gas comprising CO2 from at least one of the first and second reforming steps to produce urea.

In other words, the applicant by the present invention provides a process based on two parallel methanol production lines, each comprising a reforming section and a methanol reaction section. Each methanol reaction section providing methanol product which may be send for further processing, storage etc. as well as a gas effluent comprising nitrogen, hydrogen and unconverted carbon oxides which is highly suitable as basis for an ammonia synthesis upon methanation. Furthermore, the aspect of $CO_2$ emission from industrial plants and processes are of general concern rendering the current process of great interest as at least part of $CO_2$ from flue gas from the reforming sections is used to produce urea.

DETAILED DESCRIPTION OF THE INVENTION

As used herein the term "carbon oxides" means the components carbon monoxide and carbon dioxide.

As used herein, in the catalytic methanation of step (b) the term "by removing the unconverted carbon oxides" means converting the unconverted carbon oxides to methane. This is evidently different from carbon dioxide removal through the use of absorbers in acid gas washes, which the present invention eliminates.

Accordingly, as used herein the term "carbon dioxide removal" means highly expensive $CO_2$-removal stages in the form of acid gas wash, such as conventional MDEA and carbonate wash processes.

Preferably, in each of the first and second methanol processes, the following steps are carried out:

1) producing a methanol synthesis gas containing hydrogen, carbon oxides and nitrogen by steam reforming the hydrocarbon feedstock in a reforming section comprising a primary and a secondary reforming stage; and 2) catalytically converting the carbon oxides and hydrogen of the methanol synthesis gas in a once-through methanol synthesis stage and withdrawing an effluent comprising methanol and a gas effluent comprising nitrogen, hydrogen and unconverted carbon oxides.

In various setups, the secondary reforming stage is an air-blown secondary reforming stage.

As used herein the term "primary reforming stage" means reforming being conducted in a conventional steam methane reformer (SMR), i.e. tubular reformer with the heat required for the endothermic reforming being provided by radiation heat from burners, such as burners arranged along the walls of the tubular reformer.

As used herein the term "air-blown secondary reforming stage" means reforming being conducted in an autothermal reformer or catalytic partial oxidation reactor using air.

As used herein, the term "once-through methanol synthesis stage" means that methanol is produced in at least one catalytic reactor operating in a single pass configuration, i.e. without significant recirculation (not more than 5%, i.e. less than 5%, often 0%) of the volume flow of any gas produced in the methanol synthesis back to the at least one methanol reactor of the methanol synthesis stage, particularly the gas effluent containing hydrogen and unconverted carbon oxides.

By providing the two parallel methanol production lines and a common methanation step followed by a common ammonia synthesis, a flexible but yet very simple process is provided.

Being able to control the flow/feed of the synthesis gas from the each of the two reforming sections to each of the two methanol synthesis steps is advantageous for several reasons.

For example, the first and second once-through methanol synthesis step of the first and the second methanol processes are controlled at least by controlling the amount of syngas from the first and/or second reforming step fed to the first and/or second methanol production step.

The first and the second methanol processes may be interconnected by a synthesis gas line allowing the synthesis gas from each of the two first and second reforming steps to be distributed to each of the first and second methanol steps which for example may minimize any flaring of synthesis gas to optimize the energy consumption and thereby the operational expenditure (OPEX) and/or maximize the use of an often highly expensive reforming section by utilizing the margins in compressor design and voluntarily different deactivation cycle in the first and second methanol step.

The process may comprise further parallel methanol processes. I.e. one or more additional methanol processes may be worked in the parallel with the twin methanol process of the invention.

The parallel one, two, three or more parallel methanol processes may be interconnected by one or more synthesis gas line.

In some embodiments at least a part of the methanol from the first and/or second methanol process is converted into formaldehyde. This formaldehyde or at least part thereof may be absorbed into aqueous urea solution based on at least part of the urea to produce UFC85 or equivalent solutions. The UFC85 may be added to the urea as a coating material. UFC85 is a concentrate comprising 85% formaldehyde+ urea and 15% water.

The present application further relates to a plant for co-production of Methanol, ammonia and Urea.

A plant comprises a first and a second parallel methanol process lines, at least one common methanation reactor and at least one common ammonia synthesis step as well as a urea production section. Furthermore, the plant may advantageously comprise an interconnecting synthesis line allowing fluid communication between the first and second methanol process line.

The plant may also comprise a formaldehyde production section and/or a UFC85 production section.

With the simple and low cost process lay-out (as in EP 2192082 B1) one can afford two lines of methanol, where each one is considered large size, and gain the flexibility that comes with having two lines instead of having one big line.

Typically, the reforming section would be the most costly in terms of capital expenditure (CAPEX) and therefore very limited oversizing of this section would take place. Whereas the synthesis compressor would typically have a margin according to the relevant code and standard, and the methanol synthesis would have extra capacity when the catalyst is new and not yet deactivated. This can be utilized to gain flexibility and to reduce natural gas savings throughout the lifetime of the methanol catalyst lifetime that would be typical designed for 3-4 years. The ammonia synthesis catalyst deactivates much slower and can typically last for 20 years and will therefore not follow the catalyst lifetime cycle as the methanol synthesis catalyst. In principle, the common ammonia synthesis can be kept in operation for the whole lifetime of its catalyst by always being fed with synthesis gas from at least one of the methanol synthesis.

Further flexibility can be obtained by having an interconnecting synthesis gas line between the two front ends (synthesis gas preparation). Most likely the two Methanol synthesis would be operated in a way so they would not have catalyst replacement simultaneously. One methanol synthesis can have end-of-run (EOR) catalyst condition while the other is still in near start-of-run condition and still the total methanol synthesis capacity will be sufficient to utilize the produced synthesis gas.

This synthesis gas line can e.g. be used during start-up of the first methanol process while the second methanol process is in operation by feeding the synthesis gas from the first methanol process being started up to the second methanol process instead of flaring since the first methanol synthesis due to the start-up sequence would not be available for operation.

With methanol processes and interconnecting synthesis gas line, the costly reforming section in both methanol processes can be operated at its maximum capacity and the two methanol synthesis and one common ammonia synthesis can together convert all the synthesis gas being produced.

An ammonia synthesis loop having a capacity of 750-960 MTPD is considered as small so the most obvious advantages is to have one common ammonia synthesis line to convert the synthesis gas from two methanol synthesis lines. The total ammonia capacity would then add up to a near world class ammonia plant capacity of 1500-1920 and considerable CAPEX savings can be achieved.

Everything else that is related to the ammonia synthesis can also be in common for the two methanol lines such as (and not limited to) process air compressor, methanation section, hydrogen recovery section and ammonia recovery from purge gas. At least same relative CAPEX savings can be achieved for these sections that are considered small.

The Urea and UFC85 process steps described herein may also be used in relation with a single line methanol and ammonia co-production process such as a process/plant basically based on a single of the herein described methanol processes together with a methanation and ammonia syntheses. For example, a co-production process as described in EP 2192082 B1.

Preferably, the hydrocarbon feedstock is natural gas, for instance in the form of liquified natural gas (LNG) or substitute natural gas (SNG).

By the invention, we make direct use of the reactions governing reforming, methanol synthesis and ammonia synthesis so that methanol and ammonia can be co-produced without venting carbon dioxide being captured from the synthesis gas. The production of hydrogen by steam reforming is governed by the endothermic reaction $CH_4 + H_2O = CO + 3H_2$ while methanol synthesis in the absence of carbon dioxide is governed by the reaction $CO + 2H_2 = CH_3OH$. In the presence of carbon dioxide, methanol is otherwise also generated according to the reaction $CO_2+3\ H_2=CH_3OH+H_2O$. Ideally the feed synthesis gas for methanol production is a gas containing the highest possible molar ratio $CO/CO_2$. Ammonia synthesis occurs according to the reaction $N_2+3\ H_2=2\ NH_3$. Since when conducting the overall process, the reforming only produces 3 moles of hydrogen, while methanol synthesis already takes 2 moles of hydrogen and ammonia synthesis requires 3 moles of hydrogen, we restrict on purpose the amount of ammonia to be produced to a third in order to be able to utilize the hydrogen that is available according to ⅓ $(N_2+3\ H_2=2\ NH_3)$. Hence, in a way, by the invention we purposively promote a minimum of flexibility in the product split of methanol and ammonia.

This simple and elegant measure enables the production of about 75-80 wt % methanol and 20-25 wt % ammonia at any time in a process which is simpler and less costly than conventional ones because the process obviates the need to use highly expensive water gas shift stages for the conversion of carbon monoxide into hydrogen and carbon dioxide and also obviates the need to use highly expensive $CO_2$-removal stages, i.e. acid gas wash, such as the conventional MDEA and carbonate wash processes. Operating costs are also kept at minimum since there is no need for shift catalyst replacement and no need for solvent replenishment in the $CO_2$-removal processes. This contrasts other combined processes for the production of methanol and ammonia, such as that of JP 2000063115 where highly expensive removal of carbon dioxide via conventional $CO_2$ stripper or absorber is necessary in order to adjust the $CO_2/CO$ ratio in the synthesis gas and thereby achieve flexibility in the process. In addition, since the secondary reforming is conducted in an air-blown secondary reformer (air-blown autothermal reformer) in order to provide for the required nitrogen there is no need for expensive and massive Air Separation Units (ASU), thereby also making the process less costly than current processes where ASU plants are often required for oxygen supply in autothermal reformers and in which the attendant nitrogen production is normally used in a subsequent nitrogen wash.

The process of the present invention is environmentally friendly because there are no emissions to the surroundings of the $CO_2$ captured from the methanol and ammonia synthesis gas.

Practically all carbon monoxide (and carbon dioxide) produced in the process is used for methanol synthesis.

The process is applicable for any plant capacity including large plants producing more than 2000 MTPD ammonia and methanol, for instance 3000, 5000 MTPD or even more.

The methanol synthesis stage is preferably conducted by conventional means by passing the synthesis gas at high pressure and temperatures, such as 60-150 bars, preferably 120 bars and 150-300° C. through at least one methanol reactor containing at least one fixed bed of methanol catalyst. A particularly preferred methanol reactor is a fixed bed reactor cooled by a suitable cooling agent such as boiling water, e.g. boiling water reactor (BWR). In a specific embodiment the methanol synthesis stage in step (b) is conducted by passing the synthesis gas through one boiling water reactor and subsequently through an adiabatic fixed bed reactor, or by passing the synthesis gas through a series of boiling water reactors and subsequently through an adiabatic fixed bed reactor. Preferably the boiling water reactor is in the form of a single reactor of the condensing-methanol type which comprises within a common shell a fixed bed of methanol catalyst particles and cooling means adapted to indirectly cooling the methanol synthesis gas with a cooling agent, and which preferably operates at pressures above 90 bar and below 150 bar, more preferably above 110 bar and below 130 bar, as described in our DK patent applications PA 2008 00261 and PA 2008 00260 filed 25 Feb. 2008. The use of a methanol reactor according to these applications enables operation at pressures much higher than conventional boiling reactors which normally are about 80 bars. In addition, it enables the use of a single reactor rather than two conventional boiling water reactors, thereby significantly reducing plant costs. Furthermore, since the operating pressure in the methanol synthesis stage can be kept as high as about 120 bars or even higher there are significant savings in terms of equipment size and overall investment costs as methanol synthesis is favoured at high pressures.

Accordingly, the invention enables the operation of the methanol and ammonia synthesis section at similar operating pressures, for instance 130 bars, which implies a simplified process with significant savings in size of equipment as mentioned above. Yet it is also possible to operate at two different operating pressures, for instance 80 bars in the methanol synthesis stage and 130 bar in the ammonia synthesis stage, which implies energy savings in the methanol synthesis stage.

In step (a) the effluent containing methanol is preferably a liquid effluent. This effluent is obtained by cooling and condensation of the synthesis gas from the methanol reactors. Accordingly the process of the invention may further comprise cooling the synthesis gas withdrawn from each methanol reactor to condense methanol and passing the gas through a separator, withdrawing a bottom fraction from the separator containing the raw methanol, withdrawing an overhead fraction containing synthesis gas which is passed to the subsequent methanol reactor, and forming a single liquid effluent containing methanol by combining the bottom fractions of the separators of each reactor containing the raw methanol.

It would be understood that the term "methanol reactor" as used herein encompasses adiabatic fixed bed reactors and cooled reactors such as boiling water reactors and reactors of the condensing-methanol type which comprises within a common shell a fixed bed of methanol catalyst particles and cooling means adapted to indirectly cooling the methanol synthesis gas with a cooling agent.

Since the methanol synthesis stage is once-through, there is no need for recirculation of a part of the overhead fraction from the separator of the adiabatic fixed bed reactor back to the first methanol reactor of the methanol synthesis stage. This contrasts other combined processes for the production of methanol and ammonia, such as that of JP 2000063115 where methanol synthesis involves significant recirculation of product gas.

In step (b) the catalytic methanation stage for conversion of carbon oxides to methane is conducted in at least one methanation reactor, which is preferably an adiabatic reactor containing a fixed bed of methanation catalyst.

In step (c), the ammonia synthesis gas from the methanation stage containing the right proportion of hydrogen and nitrogen (preferably $H_2:N_2$ molar ratio of 3:1) is optionally passed through a compressor to obtain the required ammonia synthesis pressure, such as 120 to 200 bar, preferably about 130 bar. Ammonia is then produced in a conventional manner by means of an ammonia synthesis loop comprising at least one ammonia converter containing at least one fixed bed of ammonia catalyst, with interbed cooling. The effluent containing ammonia contains also hydrogen, nitrogen and inerts such as methane and argon. Ammonia may be recovered from the effluent containing ammonia as liquid ammonia by condensation and subsequent separation. Preferably, an off-gas stream containing hydrogen, nitrogen and methane is withdrawn from the ammonia synthesis stage, as also is a hydrogen-rich stream (>90 vol % $H_2$). These streams may for instance stem from a purge gas recovery unit. Preferably, this hydrogen stream is added to the methanol synthesis stage, for instance by combining with the methanol synthesis gas. The recycle of this hydrogen-rich stream enables a higher efficiency in the process as useful hydrogen is utilised in the methanol synthesis and subsequent ammonia synthesis rather than simply being used as fuel.

In order to improve the energy efficiency of the process the off-gas (purge) stream containing hydrogen, nitrogen and methane of step (c) is returned to step (a), i.e. it is returned as off-gas fuel to the reforming section of the plant, specifically to the primary reforming stage.

Plant capacity of 3000 MTPD Methanol and 750 MTPD ammonia in co-production is considered to be world class size, but even higher plant capacities are requested. By the present invention, we provide a twin methanol line plant having capacity of 2×3000 MTPD Methanol and 2×750 MTPD ammonia which can be competitive against other technologies usually considered more optimal for production of synthesis gas for methanol synthesis; such as two-step reforming or ATR.

BRIEF DESCRIPTION OF THE DRAWING

FIG. 1 shows a simplified block diagram of the process according to a specific embodiment of the invention including reforming, methanol synthesis stage, methanation stage and ammonia synthesis stage.

DETAILED DESCRIPTION OF THE PREFERRED EMBODIMENT

In first reforming section, natural gas 1 is added to primary reforming stage 20 (steam methane reformer) under addition of steam 2. The partly reformed gas is then further reformed in air-blown secondary reforming stage 21 (autothermal reformer) under addition of air 3. The methanol synthesis gas 4 containing hydrogen, carbon oxides and nitrogen is cooled in waste heat boiler(s) under the production of steam and then compressed to methanol synthesis pressure (not shown). In first methanol synthesis stage 22, the methanol synthesis gas 4 is converted in once-through operation (single-pass operation, no recirculation) under the production of a liquid effluent 5 containing methanol and a gas effluent 6 containing nitrogen, hydrogen and unconverted carbon oxides. Approximately 80 wt % of the total plant capacity goes to the production of methanol of effluent 5.

In second reforming section, natural gas 1B is added to primary reforming stage 20B (steam methane reformer) under addition of steam 2B. The partly reformed gas is then further reformed in air-blown secondary reforming stage 21B (autothermal reformer) under addition of air 3B. The methanol synthesis gas 4B containing hydrogen, carbon oxides and nitrogen is cooled in waste heat boiler(s) under the production of steam and then compressed to methanol synthesis pressure (not shown). In second methanol synthesis stage 22B the methanol synthesis gas 4B is converted in once-through operation (single-pass operation, no recirculation) under the production of a liquid effluent 5B containing methanol and a gas effluent 6B containing nitrogen, hydrogen and unconverted carbon oxides. Approximately 80 wt % of the total plant capacity goes to the production of methanol of effluent 5B.

The carbon oxides in gas effluents 6 and 6B are hydrogenated to methane in the common methanation stage 23 thereby generating an ammonia synthesis gas 7 having a $H_2$:$N_2$ molar ratio of 3:1. The ammonia synthesis gas 7 is then passed through ammonia synthesis stage 24 under the production of an effluent 8 containing ammonia and an effluent stream 9 containing hydrogen, methane and nitrogen which is treated to give two effluent streams.

First effluent stream 11 is returned as off-gas fuel to the primary reforming stage 20. Second effluent stream 10, a hydrogen-rich stream (>90 vol % $H_2$) being returned to the methanol synthesis stage 22 by combining with the methanol synthesis stream 4. Approximately 20 wt % of the total plant capacity goes to the production of ammonia in effluent 8. The plant obviates the use of Air Separation Units (ASU) as well as water gas shift and $CO_2$-removal stages.

The following table shows the temperatures, pressures and flow rates of the different streams for a process according to FIG. 1 where we are able to produce approximately 3000 MTPD methanol and 750 MTPD ammonia despite the use of a difficult feedstock. The feedstock used is heavy natural gas (85 vol % methane):

TABLE

| Position | Temp. °C. | Pressure Bar g | Flow rate/kmol/h | | | | | | |
|---|---|---|---|---|---|---|---|---|---|
| | | | $H_2O$ | $H_2$ | $N_2$ | $CH_4$ | CO | $CO_2$ | Ar |
| 4, 4B | 947 | 30.1 | 5890 | 12023 | 1414 | 419 | 3147 | 1043 | 16 |
| 6, 6B | 35 | 120.3 | 2.7 | 4574 | 1457 | 463 | 17 | 38 | 20 |
| 7 | 35 | 119.3 | | 8742 | 2914 | 1036 | | | 40 |
| 10, 10B | 35 | 32 | | 1463 | 66 | 61 | | | 4 |
| 11, 11B | 35 | 12 | | 167 | 477 | 450 | | | 16 |

The process air compressor 25 can be one common or one for each reforming section.

Stream 4/4B can be distributed to the methanol processes 22/22B depending on individual catalyst activity in order to optimize OPEX via the line 12.

Hydrogen rich stream 10/10B and off-gas 11/11B can be distributed to optimize the process requirements in reforming sections and methanol synthesis sections.

By the nature of the co-production of methanol and ammonia from natural gas, there will not be significant amount of $CO_2$ available in the process gas to be recovered for urea production. If it is desired to use part or all the ammonia production in the presented process, then $CO_2$ from the flue gas from one or more reforming sections can be recovered in a $CO_2$ removal section 27.

There would typically be sufficient of $CO_2$ in the flue gas from one reforming section to convert all the ammonia from the combined methanol section effluent gas into urea. Thereby an economy of scale can be achieved for the urea plant, section 29.

A widely used coating material in urea production is urea-formaldehyde-concentrate (UFC85) containing up to 85% urea+formaldehyde and balance is water, in order to avoid caking of urea product. The synergy for production of the coating material in this invention is clear since a small stream of methanol 16 is used to produce formaldehyde and urea solution is required for the absorption of formaldehyde to produce UFC85 or more diluted UFC products in section 28.

The invention claimed is:

1. A plant for co-producing methanol, ammonia and urea from a hydrocarbon feedstock, comprising:
    a first methanol process line for carrying out a first reforming step and a first methanol conversion step to obtain a first effluent comprising methanol and a first gas effluent comprising hydrogen, nitrogen and unconverted carbon oxides;
    a second methanol process line for carrying out a second reforming step and a second methanol conversion step to obtain a second effluent comprising methanol and a second gas effluent comprising hydrogen, nitrogen and unconverted carbon oxides;
    an interconnecting synthesis line allowing fluid communication between the first and second methanol process lines, allowing a methanol synthesis gas from each of the two first and second reforming steps to be distributed to each of the first and second methanol conversion steps;
    a catalytic methanation stage for producing ammonia synthesis gas from the first gas effluent and the second gas effluent, the ammonia synthesis gas having a $H_2:N_2$ molar ratio of approximately 3:1;
    an ammonia synthesis stage for catalytically converting the nitrogen and hydrogen of the ammonia synthesis gas to produce an effluent comprising ammonia and a purge-gas stream comprising hydrogen, nitrogen and/or methane; and
    a urea plant for reacting at least part of the effluent comprising ammonia with at least part of a flue gas comprising $CO_2$ from at least one of the first and second reforming steps to produce urea;
    wherein the first reforming step of the first methanol process line and the second reforming step of the second methanol process line are each carried out in a respective primary reforming stage and a respective secondary reforming stage, wherein the hydrocarbon feedstock is steam reformed in the respective primary reforming stage to obtain a partially reformed gas and the partially reformed gas is then further reformed under addition of air in the respective secondary reforming stage to obtain the methanol synthesis gas.

2. The plant according to claim 1, wherein the first methanol process line and the second methanol process line each further comprise a respective methanol synthesis stage for catalytically converting carbon oxides and hydrogen of the methanol synthesis gas to produce the first and second effluents comprising, respectively, methanol and a gas effluent comprising nitrogen, hydrogen and unconverted carbon oxides.

3. The plant according to claim 1, wherein the secondary reforming stage is an air-blown secondary reforming stage.

4. The plant according to claim 2, wherein the methanol synthesis stage of each of the first and second methanol process lines comprises one or more boiling water reactors for cooling the methanol synthesis gas produced by the first reforming step and the second methanol process line.

5. The plant according to claim 4, wherein the methanol synthesis stage of each of the first and second methanol process lines comprises one or more adiabatic fixed bed reactors or one or more gas cooled reactors, wherein the methanol synthesis gas is passed through the one or more boiling water reactors and subsequently through the one or more adiabatic fixed bed reactors or the one or more gas cooled reactors.

6. The plant according to claim 4, wherein the one or more boiling water reactors are each a single condensing-methanol reactor which comprises within a common shell a fixed bed of methanol catalyst particles and cooling means adapted to indirectly cooling the methanol synthesis gas with a cooling agent.

7. The plant according to claim 1, further comprising a formaldehyde production section.

8. The plant according to claim 1, further comprising a section for producing a concentrate comprising 85% formaldehyde and urea, and 15% water.

* * * * *